(12) United States Patent
Iwaya et al.

(10) Patent No.: US 8,067,585 B2
(45) Date of Patent: Nov. 29, 2011

(54) METHOD FOR PRODUCING DISULFONYL FLUORIDE COMPOUND

(75) Inventors: Masao Iwaya, Yokohama (JP); Kazuya Oharu, Yokohama (JP); Hidekazu Okamoto, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 896 days.

(21) Appl. No.: 11/865,267

(22) Filed: Oct. 1, 2007

(65) Prior Publication Data
US 2008/0091009 A1 Apr. 17, 2008

Related U.S. Application Data

(63) Continuation of application No. PCT/JP2006/306927, filed on Mar. 31, 2006.

(30) Foreign Application Priority Data

Apr. 1, 2005 (JP) .................................. 2005-106573

(51) Int. Cl.
C07D 281/02 (2006.01)
C07C 309/00 (2006.01)
C07C 313/00 (2006.01)
C07C 53/50 (2006.01)

(52) U.S. Cl. ......... 540/544; 562/825; 562/831; 562/849

(58) Field of Classification Search .................. None
See application file for complete search history.

(56) References Cited

U.S. PATENT DOCUMENTS

| 4,387,222 A | 6/1983 | Koshar |
| 4,697,011 A | 9/1987 | DesMarteau |
| 6,107,493 A | 8/2000 | Pohl et al. |
| 2005/0056809 A1 | 3/2005 | Silverman et al. |

FOREIGN PATENT DOCUMENTS

| EP | 0 211 578 A2 | 2/1987 |
| EP | 0 891 342 A1 | 1/1999 |
| EP | 1 558 716 | 8/2005 |
| JP | 0 057 327 A1 | 8/1982 |
| JP | 57-146766 | 9/1982 |
| JP | 62-26264 | 2/1987 |
| JP | 09188648 A * | 7/1997 |
| JP | 11-269115 | 10/1999 |
| JP | 2000-506132 | 5/2000 |
| JP | 2003-212809 | 7/2003 |
| JP | 2006-505654 | 2/2006 |
| WO | WO 97/31909 | 9/1997 |
| WO | WO 2004/041978 A1 | 5/2004 |

OTHER PUBLICATIONS

Werner Storzer, et al., "Two Fluorinated Fluoroxy Compounds Containing a Fluorosulfonyl Group", American Chemical Society, Inorganic Chemistry, vol. 30, No. 22, XP-002568235, 1991, pp. 4122-4125.
U.S. Appl. No. 12/699,912, filed feb. 4, 2010, Iwaya.
E. Hollitzer, et al., "The Electrochemical Perfluorination (ECPF) of Propanesulfonyl Fluorides. Part I. Preparation and ECPF of 1-Propanesulfonyl Fluoride and 1,3-Propanedisulfonyl Difluoride", Journal of Fluorine Chemistry, vol. 35, 1987, pp. 329-341.
Darryl D. DesMarteau, et al., "Synthesis and characterization of 1,2-bis (chlorosulfonyl) tetrafluoroethane and 1,2-bis (fluorosulfonyl) tetrafluoroethane", Journal of Fluorine Chemistry, vol. 89, 1998, pp. 107-109.
N. E. Petrachenko, et al., "Photoelectron He[1] spectra of fluorinated azo- and azoxy-benzenes", Journal of Fluorine Chemistry, vol. 63, 1993, pp. 85-99.
V. A. Grinberg, et al., "Investigation of the processes of electrochemical perfluoroalkylation and fluorosulphation Part 1. Electrode processes and the electrochemical perfluoroalkylation mechanism", J. Electroanalytical Chemistry, vol. 325, 1992 pp. 167-184.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to producing a disulfonyl fluoride compound easily and efficiently by utilizing coupling reaction where a compound (2) is obtained by subjecting a compound (1) wherein Y is a fluorine atom to photocoupling reaction, or subjecting a compound (1) wherein Y is a hydroxyl group, —OM$^a$ wherein M$^a$ is an alkali metal atom, or —O(M$^b$)$_{1/2}$ wherein M$^b$ is an alkaline earth metal atom to electrolytic coupling reaction, and derivatives such as the following compound (7A) are obtained from the compound (2):

$$FSO_2\text{-E-}CX_2\text{—COY} \quad (1)$$

$$FSO_2\text{-E-}CX_2\text{—}CX_2\text{-E-}SO_2F \quad (2)$$

(7A)

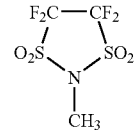

wherein E is a single bond, —O—, a $C_{1\text{-}20}$ alkylene group which may contain an etheric oxygen atom, or the like, X is a fluorine atom or the like, and Y is a fluorine atom, a hydroxyl group, or the like.

15 Claims, 2 Drawing Sheets

METHOD FOR PRODUCING DISULFONYL FLUORIDE COMPOUND

TECHNICAL FIELD

The present invention relates to an efficient method for producing a disulfonyl fluoride compound.

BACKGROUND ART

As a method for producing a disulfonyl fluoride compound, the following methods have been proposed.

(1) A method of subjecting $FSO_2(CH_2)_3SO_2F$ to electrolytic fluorination reaction to obtain $FSO_2CF_2CF_2CF_2SO_2F$ (Non-Patent Document 1).

(2) A method of subjecting cyclic tetrafluoroethylene polysulfide to oxidative ring opening with chlorine and hydrogen peroxide to obtain $ClSO_2(CF_2)_2SO_2Cl$, and fluorinating it with potassium fluoride to obtain $FSO_2(CF_2)_2SO_2F$ (Non-Patent Document 2).

(3) A method of converting $I(CF_2)_pI$ (wherein p is 3, 4 or 6) to $ClSO_2(CF_2)_pSO_2Cl$ with sodium sulfinate and chlorine and fluorinating it with potassium fluoride to obtain $FSO_2(CF_2)_pSO_2F$ (Non-Patent Document 3).

(4) A method of subjecting ethylene and a compound represented by the following formula (A) to electrolytic coupling reaction to obtain a compound represented by the following formula (C) (wherein q is 1 or 2) (Non-Patent Document 4):

$$FSO_2(CF_2)_2OCFCF(CF_3)COOH \qquad (A)$$

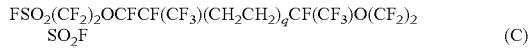

$$FSO_2(CF_2)_2OCFCF(CF_3)(CH_2CH_2)_qCF(CF_3)O(CF_2)_2SO_2F \qquad (C)$$

Further, a method of reacting $FSO_2CF_2CF_2CF_2SO_2F$ obtained by electrolytic fluorination with ammonia to obtain a cyclic perfluoroaliphatic disulfonimide ammonium salt (Patent Document 1) has been known.

Patent Document 1: JP-A-57-146766, Example 3
Non-Patent Document 1: "Journal of Fluorine Chemistry", 1987, vol. 35, pages 329 to 341
Non-Patent Document 2: "Journal of Fluorine Chemistry", 1998, vol. 89, pages 107 to 109
Non-Patent Document 3: "Journal of Fluorine Chemistry", 1993, vol. 63, pages 85 to 100
Non-Patent Document 4: "Journal of Electroanalytical Chemistry", 1992, vol. 325, pages 167 to 184

DISCLOSURE OF THE INVENTION

Problems that the Invention is to Solve

However, the above methods for producing a disulfonyl fluoride compound respectively have the following problems.

The method (1) is complicated since three step reaction from the starting material $Br(CH_2)_3Br$ is necessary to prepare $FSO_2(CH_2)_3SO_2F$. Further, the yield in the electrolytic fluorination reaction used in the method (1) is insufficient.

In the method (2), it is difficult to obtain the cyclic tetrafluoroethylene polysulfide, there are many steps, and the overall yield is low.

In the method (3), the raw material is expensive, it requires multisteps, and the overall yield is low.

In the method (4), a compound represented by the following formula (B) forms as a by-product with a yield of 30%:

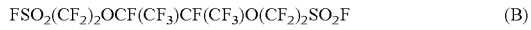

$$FSO_2(CF_2)_2OCF(CF_3)CF(CF_3)O(CF_2)_2SO_2F \qquad (B)$$

However, the object of the method (4) is to obtain the compound represented by the formula (C) by subjecting ethylene and the compound represented by the formula (A) to electrolytic coupling reaction, and when the compound represented by the formula (B) alone is to be obtained, this compound must be isolated and purified.

Further, the compound disclosed by the method (4) is only a compound wherein the terminal structure is $-CF(CF_3)COOH$. Accordingly, it has been totally unclear whether or not electrolytic coupling reaction proceeds with a compound having a terminal structure to which a carboxyl group is bonded other than the above terminal structure and having a fluorosulfonyl group.

Means to Solve the Problems

The present invention has been made to solve the above problems, and its object is to provide a method for producing a disulfonyl fluoride compound efficiently in a high yield.

Namely, the present invention provides the following:

1. A method for producing a compound represented by the following formula (2), which comprises subjecting a compound represented by the following formula (1) in which Y is a fluorine atom to photocoupling reaction or the compound in which Y is a hydroxyl group, $-OM^a$ or $-O(M^b)_{1/2}$ to electrolytic coupling reaction, to obtain the compound represented by the following formula (2):

$$FSO_2\text{-E-}CX_2\text{—COY} \qquad (1)$$

$$FSO_2\text{-E-}CX_2\text{—}CX_2\text{-E-}SO_2F \qquad (2)$$

wherein E is a single bond, an etheric oxygen atom, a $C_{1\text{-}20}$ alkylene group which may contain an etheric oxygen atom, or a group having at least one hydrogen atom in such an alkylene group substituted by a fluorine atom and/or a chlorine atom; X each independently is a hydrogen atom, a chlorine atom or a fluorine atom; and Y is a fluorine atom, a hydroxyl group, $-OM^a$ (wherein $M^a$ is an alkali metal atom) or $-O(M^b)_{1/2}$ (wherein $M^b$ is an alkaline earth metal atom).

2. A method for producing a compound represented by the following formula (3), which comprises reacting the compound represented by the formula (2) obtained by the production method as defined in the above 1 with ammonia:

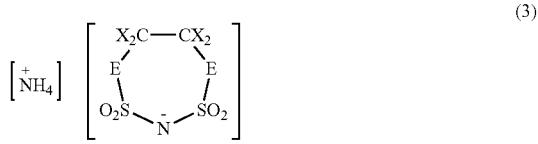

$$\left[\overset{+}{NH_4}\right]\left[\begin{array}{c}X_2C\text{—}CX_2\\E\phantom{XXX}E\\O_2S\diagdown_{\overset{|}{N}}\diagup SO_2\end{array}\right] \qquad (3)$$

wherein symbols are as defined above.

3. A method for producing a compound represented by the following formula (4), which comprises heating the compound represented by the formula (3) obtained by the production method as defined in the above 2 in the presence of a protic acid:

$$\begin{array}{c}X_2C\text{—}CX_2\\E\phantom{XXX}E\\O_2S\diagdown_{\overset{|}{NH}}\diagup SO_2\end{array} \qquad (4)$$

wherein symbols are as defined above.

4. A method for producing a compound represented by the following formula (5), which comprises reacting the compound represented by the formula (3) obtained by the production method as defined in the above 2 with a metal salt containing a n-valent metal represented by the formula M:

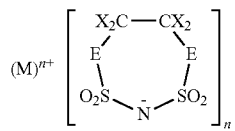  (5)

wherein E and X are as defined above, n is an integer of from 1 to 4, M is a n-valent metal, and $(M)^{n+}$ is a n-valent metal cation.

5. A method for producing a compound represented by the following formula (5), which comprises reacting the compound represented by the formula (4) obtained by the production method as defined in the above 3 with a metal salt containing a n-valent metal represented by the formula M:

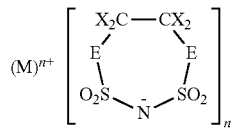  (5)

wherein E and X are as defined above, n is an integer of from 1 to 4, M is a n-valent metal, and $(M)^{n+}$ is a n-valent metal cation.

6. A method for producing a compound represented by the following formula (6), which comprises reacting the compound represented by the formula (4) obtained by the production method as defined in the above 3 with fluorine:

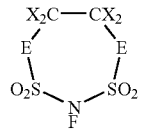  (6)

wherein symbols are as defined above.

7. A method for producing a compound represented by the following formula (6), which comprises reacting the compound represented by the formula (5) obtained by the production method as defined in the above 4 or 5 with fluorine:

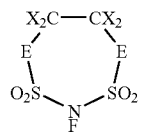  (6)

wherein symbols are as defined above.

8. A method for producing a compound represented by the formula (7) which comprises reacting the compound represented by the formula (4) obtained by the production method as defined in the above 3 with an alkylating agent having a group represented by the formula R:

  (7)

wherein E and X are as defined above, and R is a $C_{1-10}$ alkyl group which may contain an etheric oxygen atom or a nitrogen atom.

9. A method for producing a compound represented by the following formula (9), which comprises reacting the compound represented by the formula (4) obtained by the production method as defined in the above 3 with a compound represented by the following formula (8):

$$[(Z^1)^+(R^1)(R^2)(R^3)(R^4)]_k(L)^{k-} \quad (8)$$

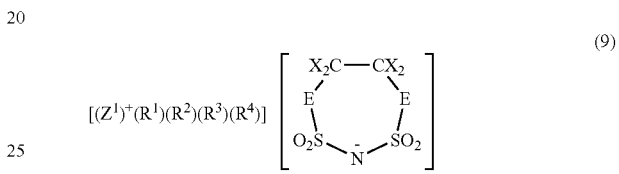  (9)

wherein E and X are as defined above; $Z^1$ is a nitrogen atom or a phosphorus atom; each of $R^1$, $R^2$, $R^3$ and $R^4$ which are independent of one another, is a $C_{1-10}$ monovalent hydrocarbon group which may contain at least one atom selected from the group consisting of an etheric oxygen atom, a nitrogen atom and a phosphorus atom, or a hydrogen atom; or two to four groups selected from $R^1$, $R^2$, $R^3$ and $R^4$ are bonded to form a cyclic structure, and when there is a remaining group not forming a cyclic structure, the remaining group is a $C_{1-10}$ monovalent hydrocarbon group which may contain at least one atom selected from the group consisting of an etheric oxygen atom, a nitrogen atom and a phosphorus atom, or a hydrogen atom; $(L)^{k-}$ is a k-valent anion; and k is 1 or 2.

10. A method for producing a compound represented by the following formula (11), which comprises reacting the compound represented by the formula (7) obtained by the production method as defined in the above 8 with a compound represented by the following formula (10):

$$Z^2(R^5)(R^6)(R^7) \quad (10)$$

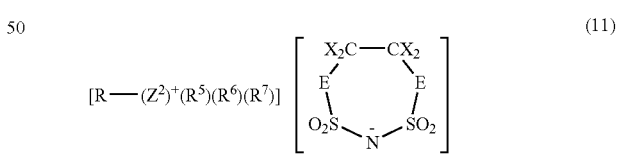  (11)

wherein E and X are as defined above; $Z^2$ is a nitrogen atom or a phosphorus atom; and each of $R^5$, $R^6$ and $R^7$ which are independent of one another, is a $C_{1-10}$ aliphatic hydrocarbon group which may contain at least one atom selected from the group consisting of an etheric oxygen atom, a nitrogen atom and a phosphorus atom, or a hydrogen atom or an aryl group; or two or three groups selected from $R^5$, $R^6$ and $R^7$ are bonded to form a cyclic structure, and when there is a remaining group not forming a cyclic structure, the remaining group is a $C_{1-10}$ aliphatic hydrocarbon group which may contain at least one atom selected from the group consisting of an etheric oxygen atom, a nitrogen atom and a phosphorus atom, or a hydrogen atom or an aryl group.

11. The production method according to any one of the above 1 to 10, wherein E is a single bond, a $C_{1-20}$ alkylene group, or a group having at least one hydrogen atom in the $C_{1-20}$ alkylene group substituted by a fluorine atom and/or a chlorine atom.

12. The production method according to any one of the above 1 to 11, wherein E is a single bond.

13. The production method according to any one of the above 1 to 12, wherein Y is a hydroxyl group, $—OM^a$ (wherein $M^a$ is an alkali metal atom) or $—O(M^b)_{1/2}$ (wherein $M^b$ is an alkaline earth metal atom).

14. The production method according to any one of the above 1 to 13, wherein Y is a hydroxyl group or $—OM^a$ (wherein $M^a$ is an alkali metal atom).

15. The production method as defined in any one of the above 1 to 14, wherein X is a fluorine atom.

16. A compound represented by the following formula (7A):

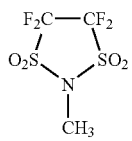

(7A)

17. A compound represented by the following formula (9A-1):

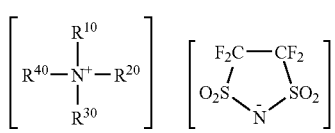

(9A-1)

wherein $R^{10}$ is a $C_{1-10}$ alkyl group, and each of $R^{20}$, $R^{30}$ and $R^{40}$ which are independent of one another, is a $C_{1-10}$ alkyl group, a hydrogen atom or an aryl group; or two to three groups selected from $R^{20}$, $R^{30}$ and $R^{40}$ are bonded to form a cyclic structure containing $N^+$, and when there is a remaining group not forming a cyclic structure, the remaining group is a $C_{1-10}$ alkyl group.

18. A method for producing a substituted ammonium, which comprises reacting a compound represented by the following formula (7) with a nitrogen-containing compound having an unshared electron pair on the nitrogen atom, to form a substituted ammonium in which the nitrogen atom in the nitrogen-containing compound is substituted by R in the formula (7):

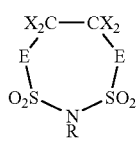

(7)

wherein symbols are as defined in the above 8.

Effects of the Invention

According to the present invention, a disulfonyl fluoride compound which has been difficult to be prepared, can be produced easily and efficiently by photocoupling reaction or electrolytic coupling reaction. Further, from the disulfonyl fluoride compound, various useful compounds can be produced.

BEST MODE FOR CARRYING OUT THE INVENTION

Figure 1:
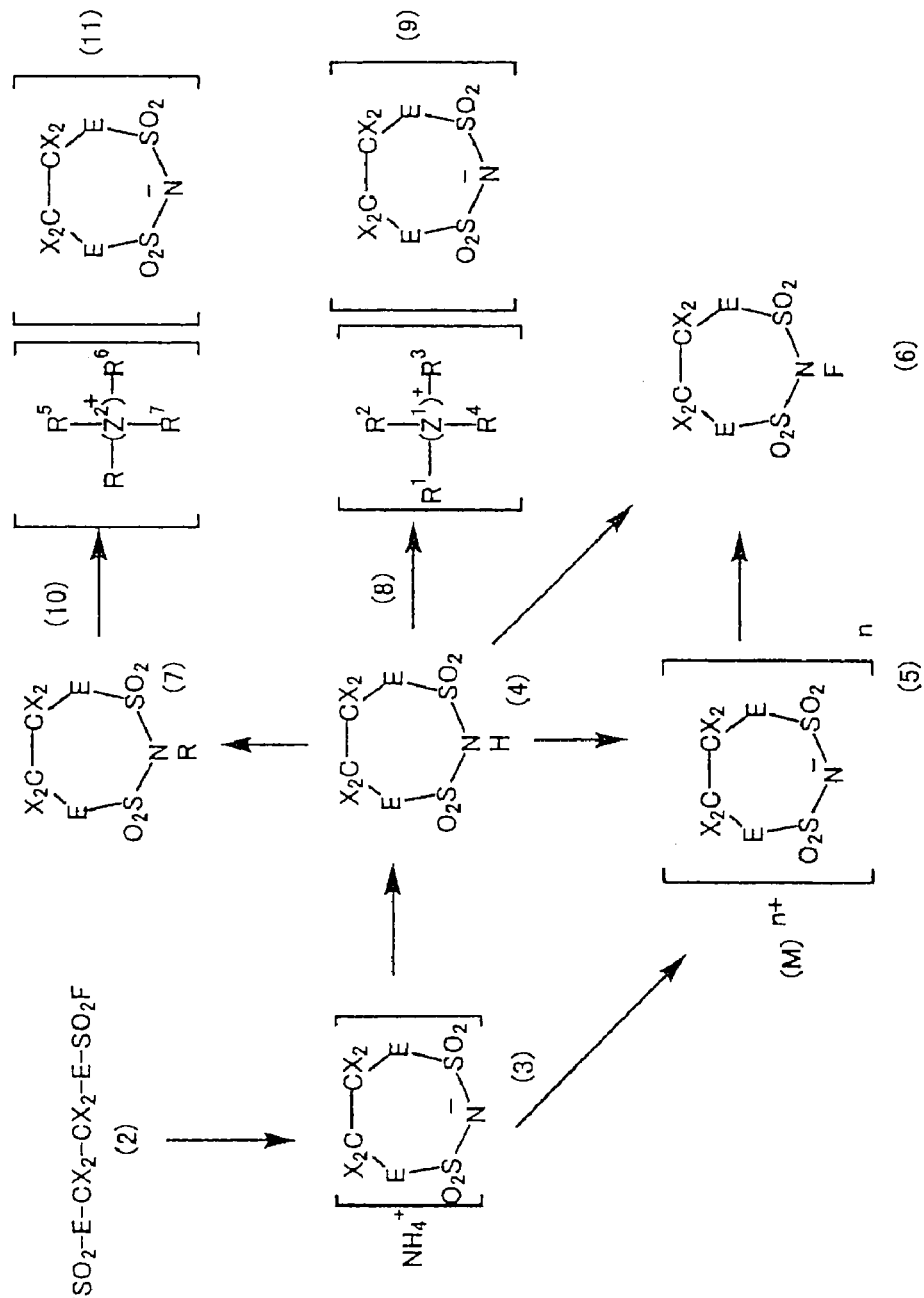
FIG. 1 is a schematic diagram illustrating a method of hydrolyzing the compound (2).

In the present specification, groups are as defined above unless otherwise specified. In the present specification, a compound represented by the formula (1) will sometimes be referred to as a compound (1). A group represented by E will sometimes be referred to as a group (E). The same applies to compounds and groups represented by other formulae. Further, the pressure is the gauge pressure unless otherwise specified.

In the present specification, E being a single bond means that in compounds in the present invention, the sulfonyl fluoride group ($—SO_2F$) and $CX_2$ are directly bonded.

In the present specification, E being an etheric oxygen atom means that in compounds in the present invention, the sulfonyl fluoride group and $CX_2$ are bonded via $—O—$ to form $FSO_2—O—CX_2—$. Specifically, the etheric oxygen atom may, for example, be an oxygen atom present between carbon atoms such as $C—O—C$ or an oxygen atom present between a sulfur atom and a carbon atom such as $S—O—C$.

In the present specification, E being a $C_{1-20}$ alkylene group which may contain an etheric oxygen atom means that in compounds in the present invention, E is a $C_{1-20}$ alkylene group or a $C_{1-20}$ alkylene group which contains an etheric oxygen atom. Such groups may have either a linear structure or a branched structure, preferably have a linear structure. In the case of a branched structure, the branched moiety is preferably a methyl group. The number of carbon atoms in such a group is preferably from 1 to 10, particularly preferably from 1 to 6.

Further, in a case where E is a group which contains an etheric oxygen atom, E preferably contains one or two etheric oxygen atoms. The etheric oxygen atom may be present between carbon atoms, may be present at the terminal moiety of the group (E) bonded to $FSO_2$, or may be present at the terminal moiety of the group (E) bonded to $CX_2$.

E being a group having at least one hydrogen atom in a $C_{1-20}$ alkylene group which may contain an etheric oxygen atom substituted by a fluorine atom and/or a chlorine atom, means a group having at least one hydrogen atom in the above alkylene group substituted by a fluorine atom and/or a chlorine atom. Such a group is preferably a $C_{1-20}$ alkylene group substituted by a fluorine atom or a $C_{1-20}$ alkylene group substituted by a fluorine atom and a chlorine atom, particularly preferably a group having all hydrogen atoms in a $C_{1-20}$ alkylene group which may contain an etheric oxygen atom substituted by fluorine atoms (i.e. a perfluorinated group).

The following groups may be mentioned as preferred embodiments of such a group. The direction of these groups is not limited, and either terminal may be bonded to $—SO_2—$ or $—CX_2—$:

$—CF_2CF_2OCF_2CF_2—$, $—CF_2CF_2CF_2OCF_2CF_2CF_2—$, $—CF_2CF_2OCF(CF_3)CF_2OCF(CF_3)—$

—$CF_2CF_2OCF(CF_3)$—

—$CF_2CF_2O$—,

—$CF_2O$—,

—$CF_2$—,

—$CF_2CF_2$—,

—$CF_2CF_2CF_2$—,

—$CF_2CF_2CF_2CF_2$—

In the present invention, E is preferably a single bond, an etheric oxygen atom, a $C_{1-20}$ alkylene group or a group having at least one hydrogen atom in the above alkylene group substituted by an atom selected from the group consisting of a fluorine atom and a chlorine atom, particularly preferably a single bond, an etheric oxygen atom or a $C_{1-20}$ perfluoroalkylene group, most preferably a single bond.

In the present invention, X each independently is preferably a chlorine atom or a fluorine atom, particularly preferably a fluorine atom. The structure at the —$CX_2$— moiety is preferably —$CF_2$—, —CFCl— or —CHF, particularly preferably —$CF_2$—.

In the present invention, Y is preferably a hydroxyl group, —$OM^a$ or —$OM^b$, and the coupling reaction in the present invention is preferably electrolytic coupling reaction.

In a case where Y is —$OM^a$ (wherein $M^a$ is an alkali metal atom), $M^a$ is preferably Na or K in view of high solubility of the compound (1) in a reaction solvent. In a case where Y is —$O(M^b)_{1/2}$ (wherein $M^b$ is an alkaline earth metal atom), $M^b$ is preferably Ca or Mg.

Compounds represented by the following formulae are mentioned as specific examples of the compound (1) in the present invention. The compound (1) wherein Y is —$O(M^b)_{1/2}$ is a compound represented by the following formula (1-M2):

$FSO_2$-E-$CX_2$—COF            (1-F), $FSO_2$-E-$CX_2$—COOH           (1-OH), $FSO_2$-E-$CX_2$—$COOM^a$       (1-M1), $(FSO_2$-E-$CX_2$—$COO)_2M^b$   (1-M2).

The compound (1) is preferably the following compound (1'):

$FSO_2$-$E^1$-$CX_2$—COY        (1')

wherein $E^1$ is a single bond, an etheric oxygen atom, a $C_{1-20}$ perfluoroalkylene group or a $C_{1-20}$ perfluoroalkylene group containing an etheric oxygen atom.

The compound (1') is the following compound (1A) when $E^1$ is a single bond, the following compound (1B) when $E^1$ is an etheric oxygen atom, the following compound (1C) when $E^1$ is a $C_{1-10}$ perfluoroalkylene group (hereinafter sometimes referred to as $E^{10}$), and the following compound (1D) when $E^1$ is a $C_{1-20}$ perfluoroalkylene group (hereinafter referred to as $E^{11}$) containing an etheric oxygen atom:

$FSO_2$—$CX_2$—COY              (1A), $FSO_2$—O—$CX_2$—COY            (1B), $FSO_2$-$E^{10}$-$CX_2$—COY     (1C), $FSO_2$-$E^{11}$-$CX_2$—COY     (1D)

$E^{10}$ preferably has from 1 to 8 carbon atoms. $E^{11}$ preferably has from 1 to 8 carbon atoms.

The following examples may be mentioned as specific examples of the compounds (1A) to (1B).

Examples of the compound (1A):

$FSO_2$—$CF_2$—COF, $FSO_2$—$CF_2$—COOH, $FSO_2$—$CF_2$—$COOM^a$, $(FSO_2$—$CF_2$—$COO)_2M^b$, $FSO_2$—CFCl—COF, $FSO_2$—CFCl—COOH, $FSO_2$—CFCl—$COOM^a$, $(FSO_2$—CFCl—$COO)_2M^b$, $FSO_2$—CHF—COF, $FSO_2$—CHF—COOH, $FSO_2$—CHF—$COOM^a$, $(FSO_2$—CHF—$COO)_2M^b$.

Examples of the compound (1B)

$FSO_2$—O—$CF_2$COF, $FSO_2$—O—$CF_2$COOH, $FSO_2$—O—$CF_2COOM^a$, $(FSO_2$—O—$CF_2COO)_2M^b$.

Examples of the compound (1C)

$FSO_2$—$CF_2CF_2$—COF, $FSO_2$—$CF_2CF_2$—COOH, $FSO_2$—$CF_2CF_2$—$COOM^a$, $(FSO_2$—$CF_2CF_2$—$COO)_2M^b$.

$FSO_2$—$CF_2CF_2OCF(CF_3)$—COOH, $FSO_2$—$CF_2CF_2OCF(CF_3)COOM^a$, $(FSO_2$—$CF_2CF_2OCF(CF_3)$—$COO)_2M^b$, $FSO_2$—$CF_2CF_2OCF(CF_3)CF_2OCF(CF_3)$—COOH, $FSO_2$—$CF_2CF_2OCF(CF_3)CF_2OCF(CF_3)$—$COOM^a$, $(FSO_2$—$CF_2CF_2OCF(CF_3)CF_2OCF(CF_3)$—$COO)_2M^b$.

Examples of the compound (1D)

$FSO_2$—$OCF_2CF_2$—COF, $FSO_2$—$OCF_2CF_2$—COOH, $FSO_2$—$OCF_2CF_2$—$COOM^a$, $(FSO_2$—$OCF_2CF_2$—$COO)_2M^b$.

In the production method of the present invention, when Y in the compound (1) is a fluorine atom, the compound (1) is subjected to photocoupling reaction to obtain the compound (2). When Y is a hydroxyl group, —$OM^a$ or —$O(M^b)_{1/2}$, the compound (1) is subjected to electrolytic coupling reaction to obtain the compound (2). In the present invention, one type of the compound (1) may be used, or at least two types of the compound (1) may be used, and it is preferred to use one type of the compound (1).

As a means of the photocoupling reaction, any known methods can be applied. It is considered that in the photocoupling reaction, radicals ($FSO_2$-E-$CX_2$·) are formed by photoirradiation, and two such radicals undergo coupling reaction to form the compound (2). A light source for photoirradiation may, for example, be a low-pressure mercury lamp, a medium-pressure mercury lamp or a high-pressure mercury lamp. The reaction temperature is preferably from $-50°$ C. to $+100°$ C., and particularly preferably from $0°$ C. to $+50°$ C. in view of the reaction efficiency. The photocoupling reaction may be conducted in the absence of a solvent or may be conducted in the presence of a solvent inert to the photoreaction (e.g. a perfluorocarbon or a perfluoroether). The reaction pressure may be any of atmospheric pressure, reduced pressure or elevated pressure and is preferably atmospheric pressure.

The electrolytic coupling reaction is a reaction of forming radicals ($FSO_2$-E-$CX_2$·) by electrolytic decarboxylation and subjecting two molecules of such radicals to coupling. As a means of the electrolytic coupling reaction, any known methods can be applied.

Further, in the electrolytic coupling reaction, a compound (1) wherein Y is a hydroxyl group and a compound (1) wherein Y is —$OM^a$ or —$O(M^b)_{1/2}$ may be used in combination. When they are used in combination, in order to improve the reaction efficiency, the amount of the compound (1) wherein Y is —$OM^a$ or —$O(M^b)_{1/2}$ is preferably from 0.01 to 1.00 time the molar amount of the compound (1) wherein Y is a hydroxyl group, particularly preferably from 0.01 to 0.10 time the molar amount.

The electrode of an electrolytic apparatus used in the electrolytic coupling reaction is preferably an electrode with a high oxidation-reduction potential (e.g. a platinum electrode). The electric current density in the electrolytic coupling reaction is preferably from 0.01 to 1.0 A/cm$^2$, and preferably from 0.02 to 0.5 A/cm$^2$ from the viewpoint of the control of heat generation and the reaction efficiency.

The electrolytic cell in the electrolytic apparatus is preferably an electrolytic cell made of glass or an electrolytic cell made of a resin (e.g. a fluororesin). Further, the electrolytic coupling reaction may be carried out employing the main body of the electrolytic cell as the anode. The reaction pressure may be any of atmospheric pressure, reduced pressure and elevated pressure, and is preferably atmospheric pressure.

The electrolytic coupling reaction may be carried out in the absence of a solvent or may be carried out in the presence of a solvent, preferably carried out in the presence of a solvent. The solvent may, for example, be an alcohol such as methanol or ethanol; a nitrile such as acetonitrile; or water. The solvents may be used alone or as a solvent mixture of at least two. The solvent is preferably a solvent mixture of water and acetonitrile.

The electrolytic coupling reaction may be carried out in a batch manner or may be carried out in a continuous reaction manner by continuously supplying the compound (1) to the electrolytic apparatus. The latter is preferred in view of a high efficiency. The reaction temperature is usually from $-20°$ C. to $+100°$ C., preferably from $-20°$ C. to $+60°$ C. Further, when E in the compound (1) contains no etheric oxygen atom, the reaction temperature is preferably $-10°$ C. to $+40°$ C. When E in the compound (1) contains an etheric oxygen atom, the reaction temperature is preferably from $-20°$ C. to $+40°$ C.

The reaction crude product containing the compound (2) obtained by the production method of the present invention may be purified by post-treatment. The post-treatment method may be a method by washing with water, extraction, chromatography, distillation, or the like. Two or more methods among these methods may be used in combination.

As a specific example of a preferred compound (2) in the present invention, the following compound (2') may be mentioned. Symbols in the formula are as defined above.

$$FSO_2\text{-}E^1\text{-}CX_2\text{—}CX_2\text{-}E^1\text{-}SO_2F \quad (2')$$

As the compound (2'), the following compounds (2A) to (2D) corresponding to the compounds (1A) to (1D) are preferred. Symbols in the formulae are as defined above.

$$FSO_2\text{—}CX_2\text{—}CX_2\text{—}SO_2F \quad (2A),$$

$$FSO_2\text{—}O\text{—}CX_2\text{—}CX_2\text{—}O\text{—}SO_2F \quad (2B),$$

$$FSO_2\text{-}E^{10}\text{-}CX_2\text{—}CX_2\text{-}E^{10}\text{-}SO_2F \quad (2C),$$

$$FSO_2\text{-}E^{11}\text{-}CX_2\text{—}CX_2\text{-}E^{11}\text{-}SO_2F \quad (2D).$$

Specific examples of the compound (2A):

$$FSO_2\text{—}CF_2\text{—}CF_2\text{—}SO_2F,$$

$$FSO_2\text{—}CClF\text{—}CClF\text{-}SO_2F,$$

$$FSO_2\text{—}CHF\text{—}CHF\text{—}SO_2F.$$

Specific examples of the compound (2B):

$$FSO_2\text{—}OCF_2\text{—}CF_2O\text{—}SO_2F$$

Specific examples of the compound (2C):

$$FSO_2\text{—}CF_2CF_2\text{—}CF_2CF_2\text{—}SO_2F$$

Specific examples of the compound (2D):

$$FSO_2\text{—}OCF_2CF_2\text{—}CF_2CF_2O\text{—}SO_2F$$

The production method of the present invention provides the production short steps, the easy operation, and the high yield. Further, the product (2) can be obtained as a single compound and the amount of impurity as by-products is small, and accordingly a complicated separation step is not necessary. Further, it was an unexpected effect that when X in the compound (1) is a fluorine atom, the radical formation and the coupling reaction of the compound (1) proceed in a higher priority than $CF_2$ carbene formation reaction of the compound (1) whereby the aimed product (2) forms with a high yield.

The compound (2) obtained by the production method of the present invention is useful as a raw material for preparation of various compounds. As examples of converting the compound (2) to other compounds, a method of hydrolyzing the compound (2) to obtain a sulfonic acid compound useful as a strong acid catalyst, and an example of obtaining a derivative of the compound (2) as exemplified in FIG. 1, may be mentioned. Symbols in compounds in FIG. 1 are as defined above.

That is, examples of converting the compound (2) to another compound, such as an example of reacting the compound (2) with ammonia to convert the compound (2) to a compound (3), an example of heating the compound (3) in the presence of a protic acid to convert the compound (3) to a compound (4), an example of reacting the compound (3) or the compound (4) with a metal salt containing a n-valent metal represented by the formula M to convert the compound (3) or the compound (4) to a compound (5), an example of reacting the compound (4) or the compound (5) with fluorine ($F_2$) to convert the compound (4) or the compound (5) to a compound (6), an example of subjecting the compound (4) and an alkylating agent having an alkyl group represented by the formula R to alkylating reaction to convert the compound (4) to a compound (7), an example of reacting the compound (7) and a compound (compound 10)) represented by the formula $Z^2 (R^5)(R^6)(R^7)$ to convert the compound (7) to a compound (11), and an example of reacting the compound (4) with a compound (compound 8)) represented by the formula $[(Z^1)^+(R^1)(R^2)(R^3)(R^4)]_k(L)^{k-}$ to convert the compound (4) to a compound (9) may be mentioned.

Further, when two or three groups selected from $R^5$, $R^6$ and $R^7$ form a cyclic structure, the cyclic structure moiety may have an aromatic cyclic structure.

The example of converting the compound (2) to a compound (3) may be carried out by a known method. For example, a method of reacting the compound (2) with ammonia in the presence of an anhydrous diethyl ether solvent may be mentioned. In the method, the reaction temperature is preferably from 20 to 30° C., and the reaction pressure is preferably atmospheric pressure. Further, a method of adding a tetrahydrofuran (THF) solution of the compound (2) to a THF solution containing liquid ammonia at a reaction temperature of about −70° C. under atmospheric pressure to react the compound (2) with ammonia.

The example of converting the compound (3) to a compound (4) may be carried out in accordance with a known method. The protic acid used in this method is preferably concentrated sulfuric acid. The reaction is carried out preferably at a reaction temperature of from 50 to 200° C. under a reaction pressure of from 50 to 40,000 Pa, particularly preferably at a reaction temperature of from 60 to 120° C. under a reaction pressure of from 150 to 4,000 Pa. The reaction is carried out preferably in a reactive distillation manner of continuously distilling off the formed compound (4).

The example of converting the compound (3) or the compound (4) to a compound (5) is carried out preferably in accordance with the method disclosed in JP-A-2000-506132. The n-valent metal represented by the formula M is selected from n-valent metals capable of forming a n-valent metal cation. n is preferably 1. Such a metal may, for example, be lithium, sodium, potassium, aluminum, magnesium, antimony, hafnium, bismuth, a rare earth, gold, silver, a copper salt, and preferably lithium which is a monovalent metal (n is 1).

A lithium metal salt containing lithium may be a salt represented by the formula $(Li^+)_m(L^B)^{m-}$, wherein $(L^B)^{m-}$ is a m-valent (wherein m is a positive integer and is preferably 1 or 2) anion, preferably a monovalent to bivalent anion. The m value agrees with the number of m indicating the number of $Li^+$ in the formula.

Specifically, the lithium salt may, for example, be $LiHCO_3$, $LiOR^a$ (wherein $R^a$ is a hydrogen atom, an alkyl group or an aryl group), $LiR^b$ (wherein $R^b$ is a hydrogen atom, an alkyl group or an aryl group), $LiN(iso-C_3H_7)_2$, $LiN(Si(CH_3)_3)_2$ or $Li_2CO_3$, preferably LiH, $LiHCO_3$, $Li_2CO_3$ or LiOH. Further, as the lithium salt, $Li_2O$ may also be employed.

The example of converting the compound (4) or the compound (5) to a compound (6) may be carried out in accordance with a known fluorination reaction (e.g. the method disclosed in J. Fluorine. Chem., 2001, vol. 112, pages 271 to 275).

R in the alkylating agent in the example of converting the compound (4) to a compound (7) is preferably a $C_{1-10}$ alkyl group, particularly preferably a $C_{1-6}$ alkyl group, particularly preferably a methyl group, an ethyl group or a propyl group. The compound (7) wherein R is an alkyl group is obtained by the alkylating reaction of the compound (4). The alkylating agent is preferably trialkyl orthoacetate, trialkyl orthoformate, alkyl halide or dialkyl sulfate. The alkylating reaction may be carried out in accordance with the method disclosed in e.g. Chem. Commun., 2003, pages 2334 to 2335.

The compound (4) is useful as a superacid catalyst for various organic reactions. Further, since the compound (4) is obtained as a solid, it is easily recovered from the reaction solution.

In the example of converting the compound (7) to a compound (11), the compound (10) is preferably the following compound (10A) or (10B), particularly preferably the compound (10A):

$N(R^5)(R^6)(R^7)$        (10A)

$P(R^5)(R^6)(R^7)$        (10B)

Each of $R^5$, $R^6$, and $R^7$ which are independent of one another, is preferably a hydrogen atom or a $C_{1-10}$ aliphatic hydrocarbon group. Otherwise, preferably $R^5$ and $R^6$ are bonded to form an alkylene group and $R^7$ is a hydrogen atom or a $C_{1-10}$ monovalent aliphatic hydrocarbon group. Further, as the compound (10A), a heterocyclic compound containing a nitrogen atom and having aromaticity may also be used.

The compound (10A) may, for example, be ammonia, methylamine, ethylamine, propylamine, butylamine, dimethylamine, diethylamine, dipropylamine, dibutylamine, methylethylamine, methylpropylamine, methylbutylamine, ethylpropylamine, ethylbutylamine, propylbutylamine, trimethylamine, triethylamine, tripropylamine, methyldiethylamine, dimethylethylamine, triphenylamine, dimethylpropylamine, diethylpropylamine, tributylamine, pyrrolidine, N-propylpyrrolidine, N-ethylpyrrolidine, N-propylpiperidine, imidazole, N-ethylimidazole, N-butylimidazole, N-hexylimidazole, N-octylimidazole, N-decylimidazole, N-dodecylimidazole, N-tetradecylimidazole, N-hexadecylimidazole, N-octadecylimidazole, 1-ethyl-2-methylimidazole, 1-butyl-2-methylimidazole, 1-hexyl-2-methylimidazole, pyridine, pyrimidine, pyridazine, pyrrole, N-methylpyrrole, N-ethylpyrrole, N-propylpyrrole, N-butylpyrrole, piperidine, N-methylpiperidine, N-ethylpiperidine, N-propylpiperidine, N-butylpiperidine, indole, N-methylindole, N-ethylindole, N-propylindole, N-butylindole, hexamethyleneimine, N-methylhexamethyleneimine, N-ethylhexamethyleneimine, N-propylhexamethyleneimine, N-butylhexamethyleneimine, oxazoline, N-methyloxazoline, N-ethyloxazoline, N-propyloxazoline, N-butyloxazoline, morpholine, N-methyl morpholine, N-ethyl morpholine, N-propyl morpholine, N-butyl morpholine, pyrroline, N-methylpyrroline, N-ethylpyrroline, N-propylpyrroline, N-butylpyrroline or hexamethylenetetramine.

As specific examples of the compound (10B), phosphine compounds wherein a nitrogen atom in the specific examples of the compound (10A) is replaced with a phosphorus atom.

The example of converting the compound (7) to a compound (11) may be carried out by a reaction means known as a salt formation reaction. The salt formation reaction is preferably a method of heating the compound in the presence of a solvent.

In the example of converting the compound (4) to a compound (9), the compound (8) is preferably the following compound (8A) or (8B), more preferably the compound (8A), particularly preferably the following compound (8A-1) or (8B-1):

$[N^+(R^1)(R^2)(R^3)(R^4)]_k(L)^{k-}$        (8A)

$[P^+(R^1)(R^2)(R^3)(R^4)]_k(L)^{k-}$        (8B)

$[N^+(R^1)(R^2)(R^3)(R^4)](L)^-$        (8A-1)

$[N^+(R^1)(R^2)(R^3)(R^4)]_2(L)^{2-}$        (8A-2)

As examples of the preferred compound (8A-1), an example wherein each of $R^1$, $R^2$, $R^3$ and $R^4$ which are independent of one another, is a hydrogen atom or a $C_{1-10}$ monovalent aliphatic hydrocarbon group, an example wherein $R^1$, $R^2$, $R^3$ and $R^4$ form a heterocyclic cation containing a nitrogen atom and having aromaticity, and an example wherein two to four groups selected from $R^1$, $R^2$, $R^3$ and $R^4$ are bonded to form an aliphatic hydrocarbon group, may be mentioned. In such a case, when there is a group which is not bonded to form an aliphatic hydrocarbon group, such a group is preferably a hydrogen atom or a $C_{1-10}$ monovalent aliphatic hydrocarbon group.

Specific examples of the cation moiety in the compounds (8A), (8A-1) and (8A-2) are disclosed in examples of the compound (9A). Specifically, $(L)^-$ may, for example, be a halogen anion, OH—, a bicarbonate anion or a nitrite anion, preferably a halogen anion or $OH^-$. Specifically, $(L)^{2-}$ may, for example, be a carbonate anion, a sulfate anion, a sulfite anion, a nitrate anion, a phosphite anion or a phosphate anion, preferably a carbonate anion or a bicarbonate anion.

The example of converting the compound (4) to a compound (11) may be carried out in accordance with a known method. The reaction is carried out preferably in the presence of a solvent. The solvent may be water or an organic solvent.

Figure 2:
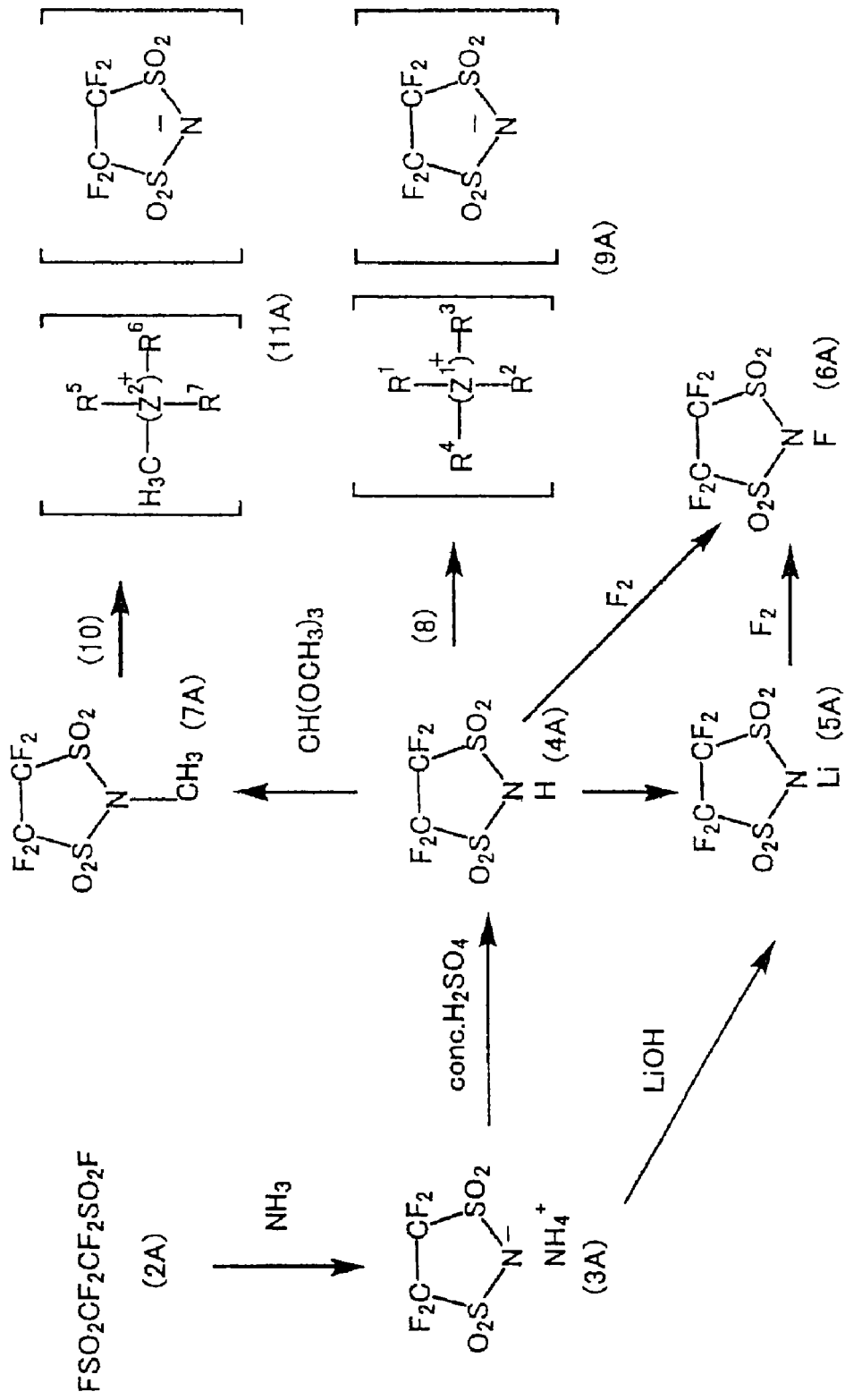
FIG. 2 is a schematic diagram illustrating a method of producing compounds (3) to (11) from the compound (2).

In the production method of the present invention, FIG. 2 may be mentioned as preferred embodiments of methods for producing compounds (3) to (11) from the compound (2).

That is, examples of converting the compound (2A) to another compound, such as an example of reacting the compound (2A) with ammonia to convert the compound (2A) to a compound (3A), an example of heating the compound (3A) in the presence of concentrated sulfuric acid under reduced pressure to convert the compound (3A) to a compound (4A), an example of reacting the compound (3A) or the compound (4A) with lithium hydroxide to convert the compound (3A) or the compound (4A) to a compound (5A), an example of reacting the compound (4A) or the compound (5A) with fluorine ($F_2$) to convert the compound (4A) or the compound (5A) to a compound (6A), an example of subjecting the compound (4A) to alkylation reaction with trimethyl orthoacetate to convert the compound (4A) to a compound (7A), an example of reacting the compound (7A) with a compound (compound (10a)) represented by the formula $Z^2$ $(R^5)(R^6)(R^7)$ to convert the compound (7A) to a compound (11A), and an example of reacting the compound (4A) with a compound (compound (8)) represented by the formula $[(Z^1)^+(R^1)(R^2)(R^3)(R^4)]_k(L)^{k-}$ to convert the compound (4A) to a compound (9A) may be mentioned.

The compound (7A) is a novel compound. Further, among the compounds (9A), the following compound (9A-1) is a novel compound.

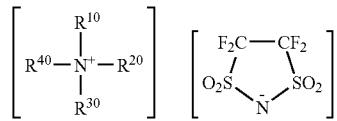
(9A-1)

Each of $R^{10}$, $R^{20}$, $R^{30}$ and $R^{40}$ which are independent of each other, is a $C_{1-10}$ alkyl group, a hydrogen atom or an aryl group. Otherwise, two to three groups selected from $R^{20}$, $R^{30}$ and $R^{40}$ may be bonded to form a cyclic structure containing $N^+$, and when there is a remaining group not forming a cyclic structure, it is an alkyl group. Preferably, all of $R^{10}$ to $R^{40}$ are alkyl groups.

Specific examples of the cation moiety ($N^+R^{10}R^{20}R^{30}R^{40}$) in the compound (9A-1) include triethylmethylammonium, diethylmethylpropylammonium, dimethylethylpropylammonium, N-methyl-N'-ethylimidazolium, N-methyl-N-propylpyrrolidinium, N-methyl-N-ethylpyrrolidinium, tetraethylammonium and tetrabutylammonium.

The compound (9A) has a small ion radius as compared with the compound (9) wherein E is —$CF_2$— and thereby has high mobility in a solution. Further, the compound (9A) is stable against a base and thereby has high solubility in an organic solvent. Further, the compound (9A) has a lower melting point and has a lower viscosity when dissolved in a solvent, than the compound (3A) wherein the cation moiety is $NH_4^+$, and is thereby excellent as an electroconductive material.

The compound (4A) itself is useful as a superacid catalyst. The compound (6A) is useful as a fluorinating reagent (DesMarteau reagent). The compound (11A) is a compound which can be useful as an electroconductive material, a reaction solvent and a heating medium.

Further, the compound (7) such as the compound (7A) can be reacted with a nitrogen-containing compound having an unshared electron pair on the nitrogen atom to produce a substituted ammonium in which the nitrogen atom in the nitrogen-containing compound is substituted by R. That is, the present invention provides a method for producing a substituted ammonium.

The nitrogen-containing compound having an unshared electron pair on the nitrogen atom may be either an aliphatic nitrogen-containing compound or an aromatic nitrogen-containing compound, and may, for example, be an amine compound selected from a primary amine, a secondary amine and a tertiary amine, or an imine compound. By reacting the compound (7) with such a nitrogen-containing compound, in the case of an amine, a cation in which the group R in the compound (7) is bonded to the nitrogen atom of the amine forms, and in the case of an imine compound, a substituted imine cation in which the nitrogen atom in the imine is substituted by the group R forms.

EXAMPLES

Now, the present invention will be described in further detail with reference to Examples. However, the present invention is not limited to such specific Examples. Compound numbers in Examples correspond to the compound numbers in FIG. 2. Gas chromatography is represented by GC, gas chromatography-mass spectrometry by GC-MS, the purity determined by the peak area ratio in GC by GC purity, the yield by GC yield, tetramethylsilane by TMS and liter by L. Further, the NMR spectrum data are represented within an apparent chemical shift range. $CF_2ClCF_2CCl_2CF_2CF_3$ is abbreviated to R419. A fluorine gas diluted to 20 vol % with a nitrogen gas is represented by a 20% fluorine gas, a methyl group by Me and an ethyl group by Et.

Example 1

Example (1) for Preparation of $FSO_2CF_2CF_2SO_2F$ (2A)

A glass separable flask (internal capacity 1.5 L) equipped with a drainage valve at the bottom and a coolant flow jacket at the main body, was provided with a mechanical stirrer, a dimroth condenser, a plunger pump for raw material feeding and a glass sheath. A thermocouple was inserted into the glass sheath. 80 Mesh platinum wires of 20 cm×10 cm were used as electrodes, and they were respectively put in a polyethylene mesh bag to prevent short circuiting, and the bags were overlaid in a tube form and installed so as to encircle an agitating element. A coolant at 0° C. was made to circulate through the dimroth condenser and the jacket.

In the flask, $FSO_2CF_2COOH$ (205.4 g), sodium hydroxide (6.0 g), acetonitrile (180 mL) and deionized water (1,200 mL) were charged, and application of an electric current was started at an electric current of 7.5 A with vigorous stirring. As the reaction proceed, the product precipitated at the bottom of the reactor. Accordingly, the product was drawn from the drainage valve at the bottom every time about 15 mL of the product was accumulated. The time of electric current application was 5 hours in total (corresponding to 1.40 F as the charge amount) and the voltage between electrodes during electric current application was from 5 to 10 V.

The amount of the recovered product was 93.3 g. The product was analyzed by GC and found to contain 93.5% of compound (2A). The GC yield was 57%, and as calculated from this value, 87.2 g of compound (2A) was obtained. The current efficiency was 47%.

Example 2

Example (2) for Preparation of Compound (2A)

The reaction was carried out in the same manner as in Example 1 except that $FSO_2CF_2COOH$ (534.0 g), acetonitrile (150 mL) and deionized water (1,000 mL) were charged, that the electric current was 13.0 A and that the electric current application time was 6.7 hours to recover 318.7 g of a product. The voltage between electrodes during electric current application was from 5 to 7 V.

The product was washed with deionized water (150 mL) three times to recover 305.5 g of a liquid. The liquid was analyzed by GC and found to contain 99.3% of compound (2A). The GC yield was 76%, and the current efficiency was 71%.

Example 3

Example for Preparation of $FSO_2CFClCFClSO_2F$ (2B)

A glass separable flask (internal capacity 50 mL) equipped with a drainage valve at the bottom and a coolant flow jacket at the main body was provided with a mechanical stirrer and a gas outlet tube. As electrodes, 80 mesh platinum wires of 2 cm×2 cm were used, and they were respectively put in polyethylene mesh bags to prevent short circuiting and installed. A coolant at 0° C. was made to circulate through the jacket on the main body.

In the flask, $FSO_2CFClCOOH$ (5.84 g), sodium hydroxide (0.15 g), acetonitrile (4.5 mL) and deionized water (30 mL) were charged, and application of electric current was started at an electric current of 0.5 A with vigorous stirring. As the reaction proceeds, the liquid product founded at the bottom of the reactor. The electric current application time was 1 hour and 36 minutes (corresponding to 30 mF as the charge amount), and the voltage between electrodes during electric current application was from 4.5 to 5 V. The product (3.10 g) was recovered and analyzed by $^{19}FNMR$ and as a result, the yield of compound (2B) was 17%.

Example 4

Example for Preparation of Compound (3A)

A 1 L autoclave which was maintained under reduced pressure was cooled to −70° C. or lower, anhydrous THF (150 mL) was charged and then ammonia (150 g) was introduced. When the internal temperature reached −70° C. or below, a solution having $FO_2SCF_2CF_2SO_2F$ (133 g) obtained in Example 1 dissolved in anhydrous THF (150 mL) was gradually dropped in the autoclave over a period of 2 hours. After the entire solution was dropped, stirring was conducted for 12 hours without controlling the internal temperature.

After completion of stirring, excess ammonia was gradually purged and when the value indicated by a pressure gauge became 0 MPa, nitrogen was introduced for one hour while stirring was continued to remove remaining ammonia.

Then, the autoclave was opened to recover a content in the form of a white slurry. White crystals attached to the wall of the autoclave were recovered by using anhydrous THF (250 mL). They were mixed and subjected to filtration under pressure, and the filtrate was concentrated to obtain crystals. The obtained crystals were dried in vacuo at 40° C. to obtain compound (3A) (127.5 g). The yield was 98%.

Example 5

Example for Preparation of Compound (4A)

The compound (3A) (78 g) obtained in Example 4 and concentrated sulfuric acid (434 g) were charged in a three-necked flask, the pressure was reduced to 400 to 533 Pa, and the temperature raising was started. When the internal temperature reached 82° C., distillation of compound (4A) started. Distillation was continued until the internal temperature reached 97° C. and as a result, compound (4A) (67.5 g) was recovered. The yield was 93%. Compound (4A) was crystals at 25° C.

Example 6

Example for Preparation of Compound (5A)

Compound (3A) (52.0 g) obtained in the same manner as in Example 4 was dissolved in THF (120 mL). Lithium hydroxide monohydrate in 1.1 times the molar amount of compound (3A) was added, followed by reflux with heating. 4 hours later, the reaction liquid was subjected to filtration to recover crystals. Water in an amount of 1.5 times the mass of the crystals was added to the crystals to dissolve them, and activated carbon in an amount of 0.2 time the mass of the crystals was added, followed by reflux with heating for 3 hours. After completion of the reflux, filtration was carried out, the filtrate was evaporated and the obtained crystals were dissolved in THF. Further, the insoluble matters were subjected to filtration, and the filtrate was evaporated again to obtain crystals. The obtained crystals were washed with n-hexane (200 mL) and dried in vacuo, and such operation was repeated twice to obtain compound (5A) (47.8 g). The yield was 96%.

Example 7

Example for Preparation of Compound (7A)

The compound (4A) (30.0 g) obtained in Example 5 was dissolved in trimethyl orthoacetate (305 g) under cooling with ice, followed by reflux with heating for 8 hours. Then, excess trimethyl orthoacetate was distilled off under atmospheric pressure, followed by vacuum distillation. Distillation of compound (7A) started under 2 MPa at an internal temperature of 50° C. Distillation was continued until the internal temperature reached 63° C. to recover a transparent and colorless liquid. The obtained liquid was stored at −30° C.

for 12 hours, whereupon crystals were precipitated, which were subjected to vacuum filtration. Crystals remaining on the filter paper were washed with HFC225 (manufactured by Asahi Glass Company, Limited, tradename: ASAHIKLIN 225) cooled with dry ice and then the crystals were recovered. The crystals were vacuum dried to obtain compound (7A) (15.0 g). The yield was 49%.

Example 8

Example (1) for Preparation of Compound (6A)

A solution having compound (4A) (0.46 g) dissolved in R419 (20 mL) was charged in a 30 mL reactor made of PFA, provided with a gas inlet and a gas outlet. The reactor was heated at 60° C., and a 20% fluorine gas was fed at a rate of 6.5 mmol/h for 1.5 hours. The reaction liquid (0.12 g) was collected, and $^{19}$FNMR analysis was carried out with 1,3-bis (trifluoromethyl)benzene as an internal standard. As a result, it was confirmed that 40% (% by area of NMR) of compound (6A) formed.

$^{19}$FNMR (283 MHz, CDCl$_3$): −13.6 (br, N—F), −115.0 (s, CF$_2$CF$_2$)

Example 9

Example (2) for Preparation of Compound (6A)

A solution having compound (4A) (3.0 g) dissolved in R419 (130 mL) was charged in a 200 mL reactor made of nickel, provided with a gas inlet and a gas outlet. The reactor was heated at 60° C., and a 20% fluorine gas was fed at a rate of 13 mmol/h for 4.9 hours. The reaction liquid was distilled under reduced pressure to obtain compound (6A) (1.3 g).

Example 10

Method for Preparing Compound (11A-1)

In a 500 ml flask, compound (7A) (35.72 g, 139 mmol), N-ethylimidazole (14.01 g, 146 mmol) and CF$_2$ClCF$_2$CFCl$_2$ (200 ml) as a solvent were added, followed by reflux for 6 hours. After cooling, the solvent and excess imidazole were distilled off, and the liquid was vacuum dried with heating at 140° C. to obtain 48.9 g of the aimed compound (11A-1). The isolation yield was 99%.

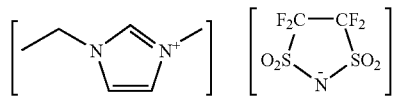
(11A-1)

Example 11

Method for Preparing Compound (11A-2)

In a 50 ml flask, compound (7A) (1.87 g, 7.3 mmol) and triethylamine (30 ml) were added, followed by reflux for 6 hours. After cooling, the solvent and excess triethylamine were distilled off, and the liquid was vacuum dried with heating at 140° C. to obtain 2.50 g of the aimed compound (11A-2). The isolation yield was 95%.

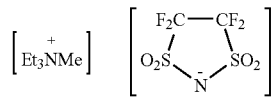
(11A-2)

Example 12

Method for Preparing Compound (9A-10)

In a 300 ml flask, compound (4A) (20.0 g, 82.3 mmol), triethylmethylammonium chloride (12.1 g, 79.9 mmol), CF$_2$ClCF$_2$CFCl$_2$ (120 ml) and acetonitrile (40 ml) were added, followed by reflux for 4 hours. After cooling, the solvent was distilled off, and the liquid was vacuum dried with heating at 140° C. The obtained white crystals were recrystallized from n-butanol and then vacuum dried to obtain 24.3 g of compound (9A-10). The isolation yield was 85%.

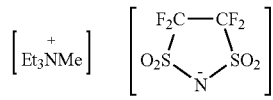
(9A-10)

INDUSTRIAL APPLICABILITY

The production method of the present invention is a method for producing a disulfonyl fluoride compound easily and efficiently without using any special apparatus or reagent and accordingly it can be an industrially useful production method. Further, the disulfonyl fluoride compound obtainable by the production method of the present invention can be converted to various derivatives useful as a superacid catalyst, an alkylating agent, etc. Accordingly, the production method of the present invention is also a method useful as a method of obtaining such derivatives in industrial scales.

The entire disclosure of Japanese Patent Application No. 2005-106573 filed on Apr. 1, 2005 including specification, claims, drawings and summary is incorporated herein by reference in its entirety.

What is claimed is:

1. A method for producing a compound represented by the following formula (2), which comprises subjecting a compound represented by the following formula (1) in which Y is a fluorine atom to photocoupling reaction or the compound in which Y is a hydroxyl group, —OMa or —O(M$^b$)$_{1/2}$ to electrolytic coupling reaction, to obtain the compound represented by the following formula (2):

FSO$_2$-E-CX$_2$—COY  (1)

FSO$_2$-E-CX$_2$—CX$_2$-E-SO$_2$F  (2)

wherein E is a single bond, an etheric oxygen atom, a C$_{1-20}$ alkylene group which may contain an etheric oxygen atom, or a group having at least one hydrogen atom in such an alkylene group substituted by a fluorine atom and/or a chlorine atom; X each independently is a hydrogen atom, a chlorine atom or a fluorine atom; and Y is a fluorine atom, a hydroxyl group, —OM$^a$ (wherein M$^a$ is an alkali metal atom) or —O(M$^b$)$_{1/2}$ (wherein M$^b$ is an alkaline earth metal atom).

2. A method for producing a compound represented by the following formula (3), which comprises reacting the compound represented by the formula (2) obtained by the production method as defined in claim 1 with ammonia:

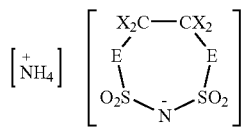 (3)

wherein symbols are as defined above.

3. A method for producing a compound represented by the following formula (4), which comprises heating the compound represented by the formula (3) obtained by the production method as defined in claim 2 in the presence of a protic acid:

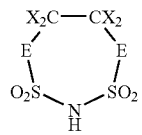 (4)

wherein symbols are as defined above.

4. A method for producing a compound represented by the following formula (5), which comprises reacting the compound represented by the formula (3) obtained by the production method as defined in claim 2 with a metal salt containing a n-valent metal represented by the formula M:

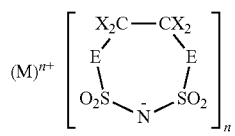 (5)

wherein E and X are as defined above, n is an integer of from 1 to 4, M is a n-valent metal, and $(M)^{n+}$ is a n-valent metal cation.

5. A method for producing a compound represented by the following formula (5), which comprises reacting the compound represented by the formula (4) obtained by the production method as defined in claim 3 with a metal salt containing a n-valent metal represented by the formula M:

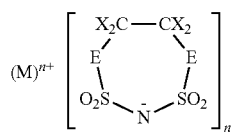 (5)

wherein E and X are as defined above, n is an integer of from 1 to 4, M is a n-valent metal, and $(M)^{n+}$ is a n-valent metal cation.

6. A method for producing a compound represented by the following formula (6), which comprises reacting the compound represented by the formula (4) obtained by the production method as defined in claim 3 with fluorine:

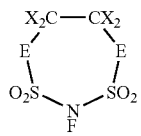 (6)

wherein symbols are as defined above.

7. A method for producing a compound represented by the following formula (6), which comprises reacting the compound represented by the formula (5) obtained by the production method as defined in claim 4 with fluorine:

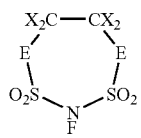 (6)

wherein symbols are as defined above.

8. A method for producing a compound represented by the formula (7), which comprises reacting the compound represented by the formula (4) obtained by the production method as defined in claim 3 with an alkylating agent having a group represented by the formula R:

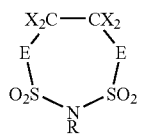 (7)

wherein E and X are as defined above, and R is a $C_{1-10}$ alkyl group which may contain an etheric oxygen atom or a nitrogen atom.

9. A method for producing a compound represented by the following formula (9), which comprises reacting the compound represented by the formula (4) obtained by the production method as defined in claim 3 with a compound represented by the following formula (8):

 (8)

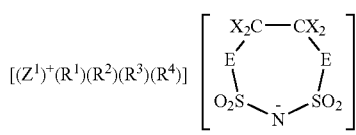 (9)

wherein E and X are as defined above; $Z^1$ is a nitrogen atom or a phosphorus atom; each of $R^1$, $R^2$, $R^3$ and $R^4$ which are independent of one another, is a $C_{1-10}$ monovalent hydrocarbon group which may contain at least one atom selected from the group consisting of an etheric oxygen atom, a nitrogen atom and a phosphorus atom, or a hydrogen atom; or two to four groups selected from $R^1$, $R^2$, $R^3$ and $R^4$ are bonded to form a cyclic structure, and when there is a remaining group not forming a cyclic structure, the remaining group is a $C_{1-10}$ monovalent hydrocarbon group which may contain at least one atom selected from the group consisting of an etheric oxygen atom, a nitrogen atom and a phosphorus atom, or a hydrogen atom; $(L)^{k-}$ is a k-valent anion; and k is 1 or 2.

10. A method for producing a compound represented by the following formula (11), which comprises reacting the compound represented by the formula (7) obtained by the production method as defined in claim 8 with a compound represented by the following formula (10):

$$Z^2(R^5)(R^6)(R^7) \quad (10)$$

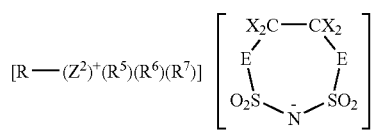
(11)

wherein E and X are as defined above; $Z^2$ is a nitrogen atom or a phosphorus atom; and each of $R^5$, $R^6$ and $R^7$ which are independent of one another, is a $C_{1-10}$ aliphatic hydrocarbon group which may contain at least one atom selected from the group consisting of an etheric oxygen atom, a nitrogen atom and a phosphorus atom, or a hydrogen atom or an aryl group; or two or three groups selected from $R^5$, $R^6$ and $R^7$ are bonded to form a cyclic structure, and when there is a remaining group not forming a cyclic structure, the remaining group is a $C_{1-10}$ aliphatic hydrocarbon group which may contain at least one atom selected from the group consisting of an etheric oxygen atom, a nitrogen atom and a phosphorus atom, or a hydrogen atom or an aryl group.

11. The production method according to claim 1, wherein E is a single bond, a $C_{1-20}$ alkylene group, or a group having at least one hydrogen atom in the $C_{1-20}$ alkylene group substituted by a fluorine atom and/or a chlorine atom.

12. The production method according to claim 1, wherein E is a single bond.

13. The production method according to claim 1, wherein Y is a hydroxyl group, —$OM^a$ (wherein $M^a$ is an alkali metal atom) or —$O(M^b)_{1/2}$ (wherein $M^b$ is an alkaline earth metal atom).

14. The production method according to claim 1, wherein Y is a hydroxyl group or —$OM^a$ (wherein $M^a$ is an alkali metal atom).

15. The production method as defined in claim 1, herein X is a fluorine atom.

* * * * *